US00RE39537E

(19) United States
(12) Reissued Patent
Cruce et al.

(10) Patent Number: US RE39,537 E
(45) Date of Reissued Patent: Apr. 3, 2007

(54) SIGNAL GENERATION AND MIXING ELECTRONICS FOR FREQUENCY-DOMAIN LIFETIME AND SPECTRAL FLUOROMETRY

(75) Inventors: Tommy Clay Cruce, Leander, TX (US); William H. Hallidy, Austin, TX (US); Robert C. Chin, Austin, TX (US)

(73) Assignee: Systems & Processes Engineering Corporation, Austin, TX (US)

(21) Appl. No.: 10/035,461

(22) Filed: Nov. 9, 2001

Related U.S. Patent Documents

Reissue of:
(64) Patent No.: 5,981,957
Issued: Nov. 9, 1999
Appl. No.: 08/958,779
Filed: Oct. 27, 1997

(51) Int. Cl.
*G01N 21/64* (2006.01)

(52) U.S. Cl. ..... 250/458.1; 250/459.1; 356/317

(58) Field of Classification Search ..... 250/458.1, 250/459.1, 461.1; 356/317, 318
See application file for complete search history.

(56) References Cited

U.S. PATENT DOCUMENTS 5,196,709 A * 3/1993 Berndt et al.

OTHER PUBLICATIONS

Weber, G., Resolution of the Florescence Lifetimes in a Heterogeneous System by Phase and Modulation Measurements, J. Phys. Chem., 85, (1981) pp. 949–953.*

Lackowicz, J.R., Analysis of Fluorescence Decay Kinetics from Variable–Frequency Phase Shift and Modulation Data, Biophys. J., 46 (1984) pp. 463–477.*

Burdick, D.S. et al., Resolution of Multicomponent Fluorescent Mixtures by Analysis of the Excitation–Emission–Frequency Array, J. Chemometrics, 4 (1990) pp. 15–28.*

* cited by examiner

*Primary Examiner*—Scott J. Sugarman
*Assistant Examiner*—Richard Hanig

(57) ABSTRACT

The present invention additionally comprises a method and apparatus for generating and mixing signals for frequency-domain lifetime and spectral fluorometry. The present invention comprises a plurality of signal generators that generate a plurality of signals where the signal generators modulate the amplitude and/or the frequency of the signals. The present invention uses one of these signals to drive an excitation signal that the present invention then directs and transmits at a target mixture, which absorbs the energy from the excitation signal. The property of fluorescence causes the target mixture to emit an emitted signal that the present invention detects with a signal detector. The present invention uses a plurality of mixers to produce a processor reference signal and a data signal. The present invention then uses a processor to compare the processor reference signal with the data signal by analyzing the differences in the phase and the differences in the amplitude between the two signals. The processor then extracts the fluorescence lifetime and fluorescence spectrum of the emitted signal from the phase and amplitude information using a chemometric analysis.

25 Claims, 6 Drawing Sheets

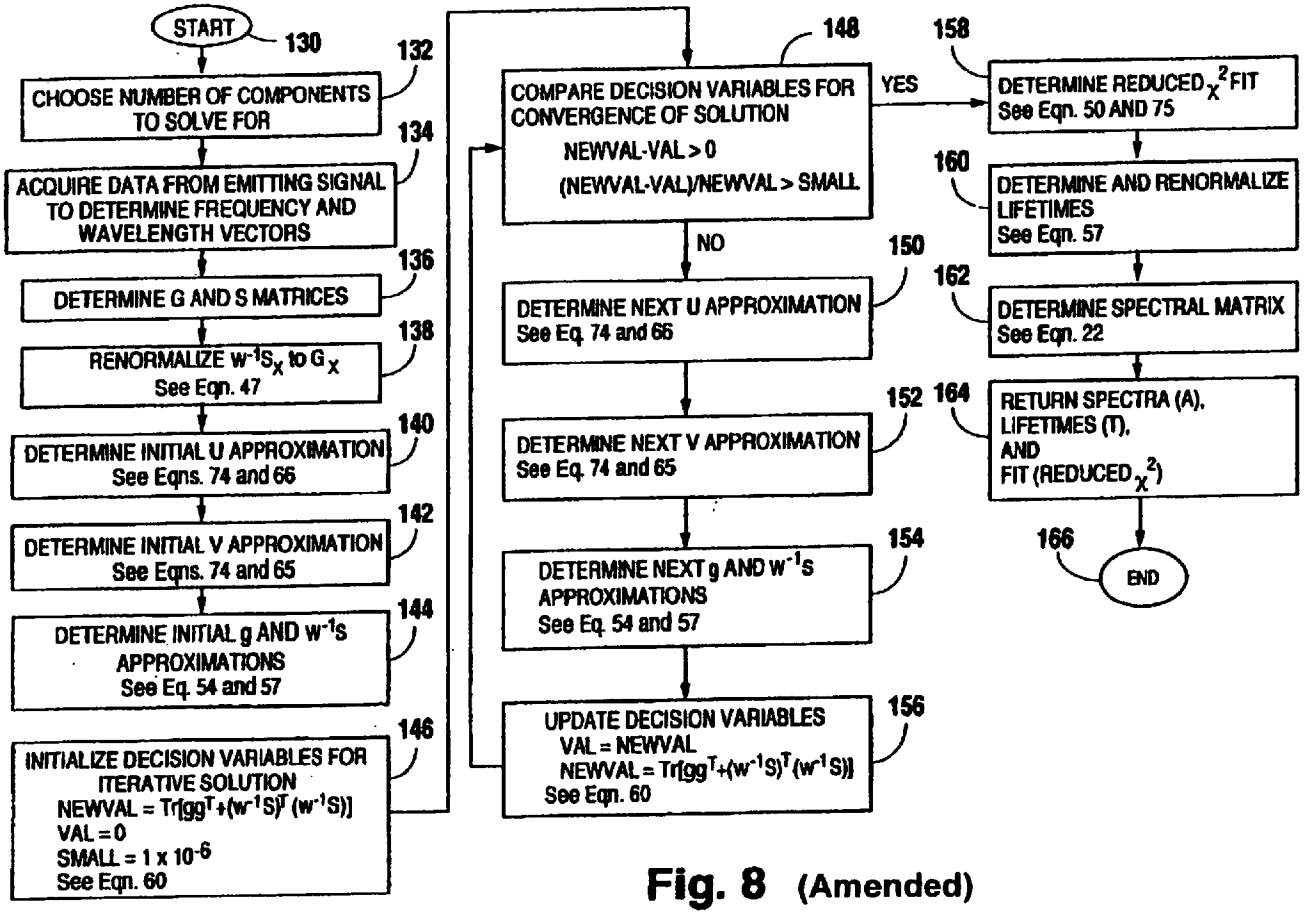
Fig. 8 (Amended)

SIGNAL GENERATION AND MIXING ELECTRONICS FOR FREQUENCY-DOMAIN LIFETIME AND SPECTRAL FLUOROMETRY

Matter enclosed in heavy brackets [ ] appears in the original patent but forms no part of this reissue specification; matter printed in italics indicates the additions made by reissue.

The U.S. Government has a paid-up license to certain technologies disclosed in this invention and the right in limited circumstances to require the patent owner to license others on reasonable terms as provided for by the terms of the following contracts: NAS1-20426 and NAS1-20162 awarded by NASA; DAAH01-91-R198 awarded by US Army Missile Command; DAAL06-92-C-0014 and DAAD07-91-C-0127 awarded by US Army White Sands Missile Range; DAA15-93-C-0034 and DAAM01094-C-0033 awarded by US Army Chemical and Biological Defense Agency; and F41624-95-C-6010 and F41627-97-C-6029 awarded by US Air Force Armstrong Laboratory.

BACKGROUND OF THE INVENTION

1. Field of the Invention

The present invention generally relates to fluorescence measurements. More specifically, the present invention relates to frequency domain measurements of the fluorescence lifetime and the fluorescence spectrum.

2. Description of the Related Art

The process of fluorescence occurs when a substance, such as a molecule, absorbs light at one wavelength (or energy), and then emits light at a longer wavelength (or lower energy). A slight time delay occurs from when the substance absorbs light and when the substance re-emits light at the longer wavelengths. This time delay is known as the fluorescence lifetime.

FIG. 1 depicts the fluorescence process substantially for a diatomic molecule, which is a molecule that is comprised of two atoms. There are several "types" of energy that are internal to a diatomic molecule, one of which is vibrational energy. The classic example of vibrational energy is imaging the two atoms connected together by a spring where the atom oscillate back and forth along the axis of the spring. As the two atoms approach each other, the experience repulsion due to the proximity of their negatively charged electron clouds. As the atoms pull apart from one another, they experience an attraction that one can imagine as the result of the attractive forces between the positively charged nucleus of one atom for the negatively charged electron cloud of the other atom, and vice versa. The distance between the two atoms is known as the internuclear distance, which constantly changes as the two atoms oscillate back and forth. As the intranuclear distance decreases, a rise in potential energy occurs due to the repulsive forces; as the intermediate distance increases, a rise in potential energy again occurs due to the attractive forces. FIG. 1 illustrates this difference in potential energy by line 11 in line potential energy "well" 10 and by line 13 in the potential energy "well" 12 where line 11 and 13 plot the potential energy as a function of internuclear distance.

A group of horizontal lines 20, 22, and 24 appear in each of the potential energy wells 10 and 12. Each horizontal line represents the individual vibrational energy states possible for the diatomic molecule. Quantum mechanics requires that the vibrational frequency of the spring be within certain values. In other words, the spring may oscillate at frequency 'a', and the spring may oscillate at frequency 'b', but it is a physical impossibility for the spring to oscillate at any frequency between 'a' and 'b'. In FIG. 1, any two adjacent horizontal lines would represent 'a' and 'b'.

The different potential energy wells 10 and 12 represent another type of energy in the diatomic molecule: electronic energy. Different electronic energies occur when the molecule absorbs energy in such a fashion that it causes an electron to improve to a higher energy configuration within the molecule. The classical example of the energy absorption is the 'changing the spring' that connects the two atoms. If we "add" electronic energy to the potential energy well 10, the energy raises the potential energy well 10 to the energy level of potential energy well 12.

With this background, we can use FIG. 1 to describe the process of fluorescence and fluorescence lifetime for a diatomic molecule. The example molecule is originally in a state depicted by the lower potential energy well 10. The molecule absorbs a photon of the correct amount of energy that induces an electron to move to a higher electronic energy state, represented by the upper potential energy well 12. The diatomic molecule also tends to undergo a change from a 'lower vibrational state' (the horizontal line 20 and 22) in the lower potential well 10 to a higher vibrational state in the upper potential well 12. This initial excitation of the molecule is shown by line 14. Through any one of numerous possible processes, the higher vibrational state 24 in the upper well decays to a lower vibrational state 22 in the upper well (as shown by line 18). The process of non-radiative decay to a lower vibrational energy level in the upper well occurs very rapidly. After the non-radiative vibrational relaxation, the electron will want to return or revert back to a lower energy state as shown by line 16 (in other words, the electron wants to move back to where it was before the whole process started), and in so doing, the molecule emits a photon of light (with a lesser amount of energy than the excitation photon). This lowering of the energy state and the In practice, we typically probe many different types of molecules at once with the excitation light pulse. FIG. 2 illustrates the case where a single short excitation pulse of light 30 is absorbed by a sample of identical molecules all at once. The fluorescence decay curve 32 resulting from a typical fluorescence response of a sample of identical molecules is exponential in nature because not all of the identical molecules emits its fluorescence photon at precisely the same time. The exponential decay follows a mathematical function so that we can calculate the fluorescence lifetime, $\tau$:

$$[I(t)=I_0\cdot e^{-(t-5_0)/\tau}]$$

$$I(t)=I_0\cdot e^{-(t-t_0)/\tau}$$

where $t_0$ is the time *of* the excitation pule, $I_0$ is the initial fluorescence and I(t) is the observed fluorescence intensity as a function of time. emission of a photon is the process of fluorescence. The process of emitting the photon has an associated time delay, which is the fluorescence lifetime.

In the cases with multiple molecular types (where more than one lifetime decay is presented within a sample of a target mixture), the exponential decay seen in FIG. 2 would appear as a sum of exponential functions. Prior art fluoremeters typically use a type of time-correlated (or time-resolved) system that count the emitted photons (from an excited molecule) in order to measure the fluorescence lifetime. Other prior art systems add the ability to take the fluorescence lifetime measurements in the frequency domain by modulating the dynode of a photomultiplier tube, followed by a mixing and correlation procedure. These prior art systems are cumbersome, time consuming, and complicated to operate. The present invention overcomes the limitations of the prior art systems by utilizing a novel technique to measure the fluorescence lifetime and spectrum. Instead of irradiating the target sample with a single short pulse of light (photon counting), the present invention continuously irradiates the target sample with a light source whose amplitude modulation frequency is stepped with time. This technique allows us to use a chemometric analysis to automatically extract the lifetimes from the 'phase delay' and 'intensity vs. frequency' characteristics of the emitted light.

SUMMARY OF THE INVENTION

The present invention is a system for chemometric analysis for the extraction of the individual fluorescence spectrum and fluorescence lifetime from a target mixture. The present invention comprises a processor with an apparatus for generating an excitation signal to transmit at a target mixture and an apparatus for detecting the emitted signal from the target mixture. One embodiment of the present invention uses a processor that comprises a computer that extracts the individual fluorescence spectrum and lifetime measurements from the frequency and wavelength data acquired from the emitted signal. The present invention first determines the G and S matrices from the frequency and wavelength vectors. A renormalization of $w^{-1}S_x$ to $G_x$ occurs next due to the differences in units. Next, the present invention determines the initial U, V, g and $w^{-1}$s approximation. The present invention uses an iterative solution that first requires the initialization of the decision variables including $\eta$. The iterative solution compares the decision variables for convergence to see if further approximation determinations of the U, V, g and $w^{-1}$s are necessary. When the solution converges, the present invention then determines the reduced best fit error for the analysis of the individual fluorescence lifetime and the fluorescence spectrum. And finally, the system of the present invention extracts individual component fluorescence lifetime and fluorescence spectra from the emitted signal of the target mixture.

The present invention additionally includes a method and apparatus for generating and mixing signals for frequency-domain lifetime and spectral fluorometry. The present invention comprises a signal generator that generates a driving/references signal that modulates the amplitude and/or the frequency of the driving/reference signal over time and a signal generator that generates the mixing signal that modulates the amplitude and/or the frequency of the mixing signal over time. The driving/reference signal generator drives an excitation signal generator that generates the excitation signal. The present invention then directs and transmits the excitation signal at a target mixture, which absorbs the energy from the excitation signal. The property of fluorescence causes the target mixture to emit an emitted signal that the present invention detects with a signal detector. The present invention uses a mixer that mixes the emitted signal with the driving/reference signal to produce a processor reference signal. Another mixer mixes the emitted signal with the mixing signal to produce a data signal. The present invention then uses a processor to compare the processor reference signal with the data signal by analyzing the differences in the phase and the differences in the amplitude between the two signals. The processor then extracts the fluorescence lifetime and fluorescence spectrum of the emitted signal from the phase and amplitude information using a chemometric analysis.

BRIEF DESCRIPTION OF THE DRAWINGS

To further aid in understanding the invention, the attached drawings help illustrate specific features of the invention and the following is a brief description of the attached drawings:

FIG. 8 is a block diagram of an embodiment of the present invention for a chemometric analysis of the emitted signal to determine the fluorescence spectrum and fluorescence lifetimes.

DETAILED DESCRIPTION OF THE INVENTION

The present invention is a system for chemometric analysis for the extraction of the individual component fluorescence spectra and fluorescence lifetimes from a target mixture. Additionally, the present invention is a method and apparatus for generating and mixing signals for frequency-domain lifetime and spectral fluorometry. This disclosure describes numerous specific details that include specific processes, structures, and circuits in order to provide a thorough understanding of the present invention. For example, the present invention describes the extraction of the fluorescence spectra and fluorescence lifetimes from a target mixture. However, the practice of the present invention includes the extraction or analysis of other physical properties of a target mixture other than the previously described ones. One skilled in the art will appreciate that one may practice the present invention without these specific details. Additionally, this disclosure does not describe some well known processes such as Fourier transforms, eigenequations, eigenfunctions, eigenvalues, transforms, or best fit analysis in detail in order not to obscure the present invention.

Figure 1:
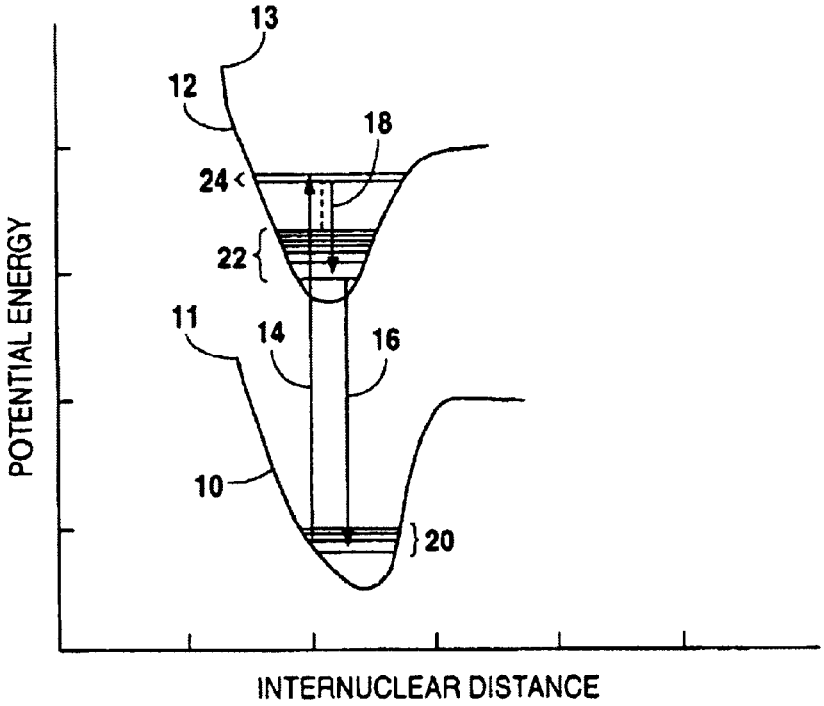
FIG. 1 illustrates the fluorescence process for a diatomic molecule.
Figure 2:
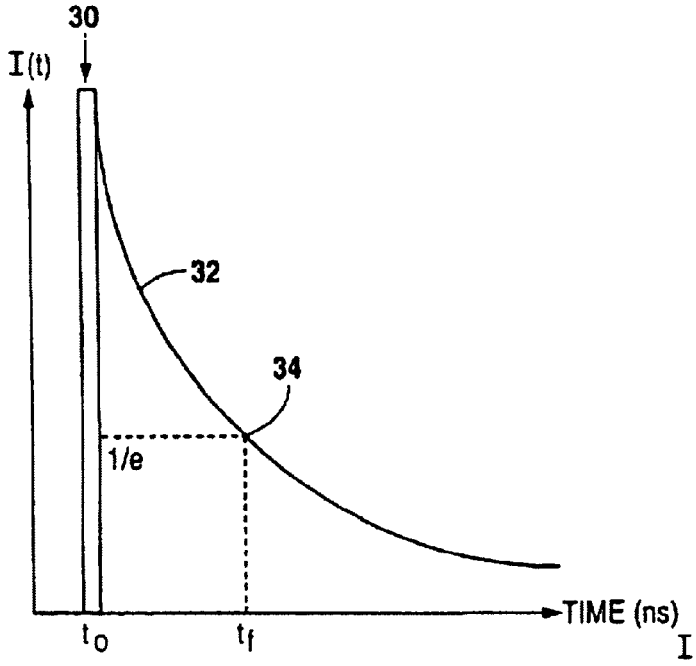
FIG. 2 illustrates the absorption and emission of energy for the fluorescence process.
Figure 3:
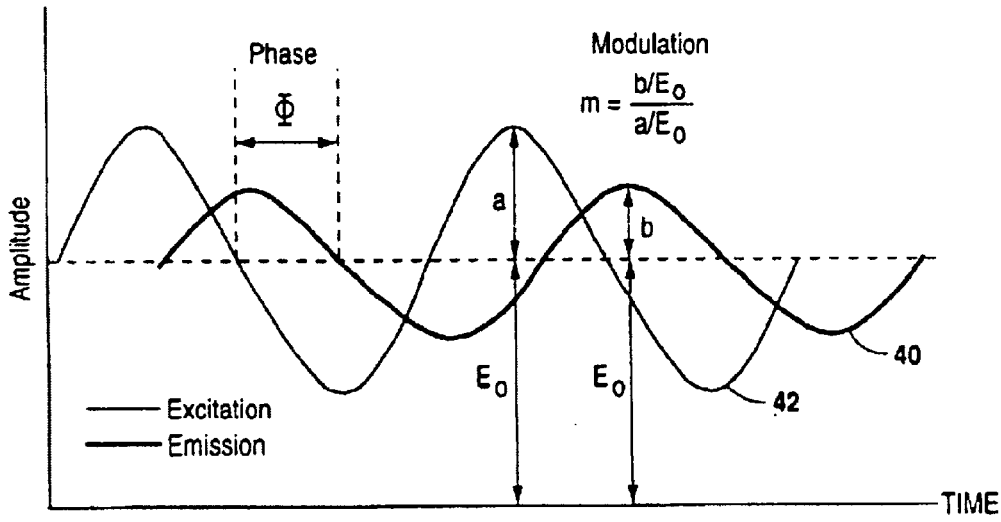
FIG. 3 illustrates the chemometric extraction process of the present invention for fluorescence spectrums and lifetimes.

The present invention utilizes a novel system that uses a chemometric analysis to determine the fluorescence lifetimes and the fluorescence spectra of a target mixture. Instead of irradiating the target sample with a single short pulse of light (photon counting) as other prior art systems, the present invention continuously irradiates the target mixture with a light source whose amplitude modulation frequency is stepped with time. FIG. 3 illustrates the process of the present invention. The excitation light or signal 42, which is the signal the present invention uses to continuously irradiate the target mixture, is amplitude and phase modulated in a sinusoidal fashion. As previously discussed, the emitted signal 40 is the photon emitted (emission intensity) from the molecule as a result of the fluorescence process. The emitted signal 40 will appear as a delayed sinusoid-intensity light of a longer wavelength. Embedded within the emitted signal is the information necessary to extract the fluorescence lifetime and spectrum. However, one must use a chemometric analysis to extract the fluorescence lifetimes from the 'phase delay Φ' of the emitted light (compared to excitation signal) and the 'intensity vs. wavelength' (or spectrum) characteristics of the emitted light (compared to the excitation signal).

Figure 4:
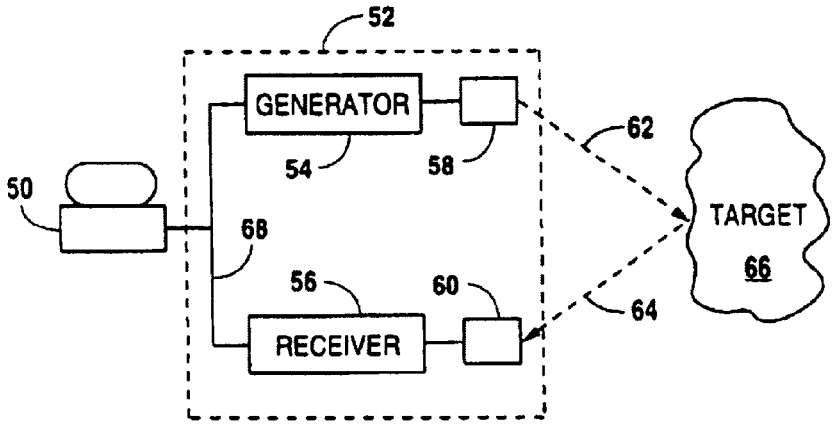
FIG. 4 is a block diagram of the present invention.

FIG. 4 is a block diagram of the apparatus component of the present invention. A processor 50 couples to a data acquiring component 52 through a data input/output path 68. The preferred embodiment of the processor 50 comprises a computer. The data acquiring component comprises a generator component 54 and a receiver component 56. Coupled to the generator component 54 is an excitation signal generator 58. The excitation signal generator produces an excitation signal (or light photon) that is transmitted to a target mixture 66. The target mixture 66 absorbs the electronic energy of the excitation signal as the molecules of the target mixture move to a higher electronic energy state. During the fluorescence process, the molecules of the target mixture emit photons (an emitted signal 64) as the molecules move to a lower electronic energy state. A detector 60 detects the emitted signal 64 from the target mixture 66. Coupled to the detector is the receiver component 56, which processes the returned emitted signal 64 into a reference signal and a data signal for the processor 50. The processor 50 then uses a chemometric analysis to determine the individual fluorescence spectrum and fluorescence lifetime of one or more fluorophores within the target mixture 66.

Figure 5:
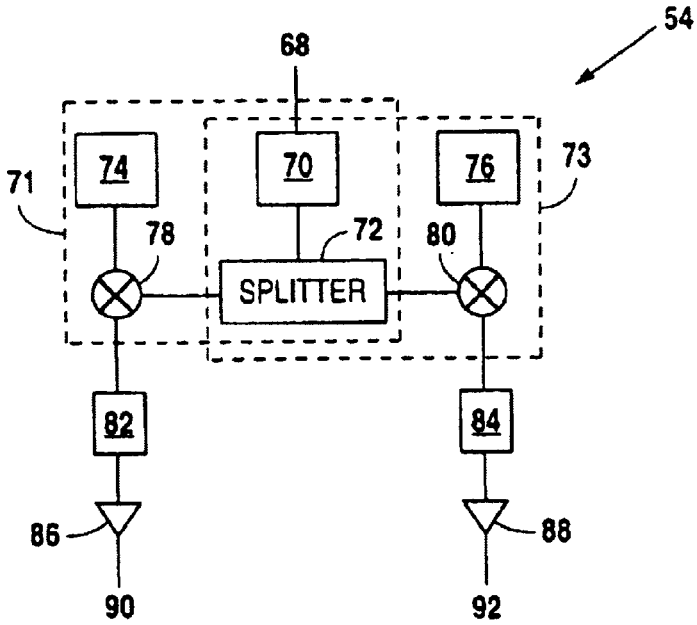
FIG. 5 is a block diagram of a component of the present invention for generating an excitation signal.

FIG. 5 is a block diagram of the generator component 54 of the present invention for generating the excitation signal. The present invention uses heterodyning techniques to produce two sinusoidal RF signals, a driving/reference signal 90 and a mixing signal 92. The present invention modulates the frequency of the two signals from 10 MHz to 200 MHz. One skilled in the art will appreciate that the present invention could vary the signals over a much larger frequency range. The preferred embodiment of the present invention generates the two signals with a frequency difference of 10 kHz. Another embodiment of the present invention generates the two signals using an adjustable offset frequency where the offset frequency is set through [to ]the present invention's control software.

Referring back to FIG. 5, the present invention generates the driving/reference signal with a driving/reference signal generator 71 and generates the mixing signal with a mixing signal generator 73. The driving/reference signal generator 71 comprises an oscillator 74, a phase-locked-loop (PLL) 70, a mixer 78, and a signal splitter 72. The mixing signal generator 73 comprises an oscillator 76, the phase-locked-loop (PLL) 70, a mixer 80, and the signal splitter 72. The present invention generates the two signals by mixing a signal from the PLL 70 with the signals from the two fixed oscillators 74 and 76. The preferred embodiment of the present invention operates oscillator 74 at 290 MHz and oscillator 76 at 290.01 MHz. One skilled in the art will appreciate that other operating frequencies for oscillators are possible. The preferred embodiment of the present invention can set the output of the PLL 70 to a frequency ranging from 300 to 500 MHz, which the present invention through the digital I/O datapath 68.

Coupled to the driving/reference signal generator 71 is a filter 82 and an amp 86. The filter 82 filters out any unwanted components from the driving/reference signal, and the amp 86 provides additional gain to the signal if necessary. Coupled to the mixing signal generator 73 is a filter 84 and an amp 88. The filter 82 filters out any unwanted components from the mixing signal, and the amp 86 provides additional gain to the signal if necessary. The present invention uses the driving reference signal 90 as a phase and amplitude reference signal on the receiver component 56 (of FIG. 6). And, the present invention sends the mixing signal 92 to the receiver component 56 where it is split.

The present invention uses the driving/reference signal 90 to directly drive and modulate an excitation signal generator 58 (of FIG. 7) that may comprise a laser diode, a light emitting diode (LED), or a Deuterium lamp. The present invention can also use the modulation to directly modulate an electro-optic crystal for use in external modulation of gas laser sources or other continuous emitting excitation light sources.

Figure 6:
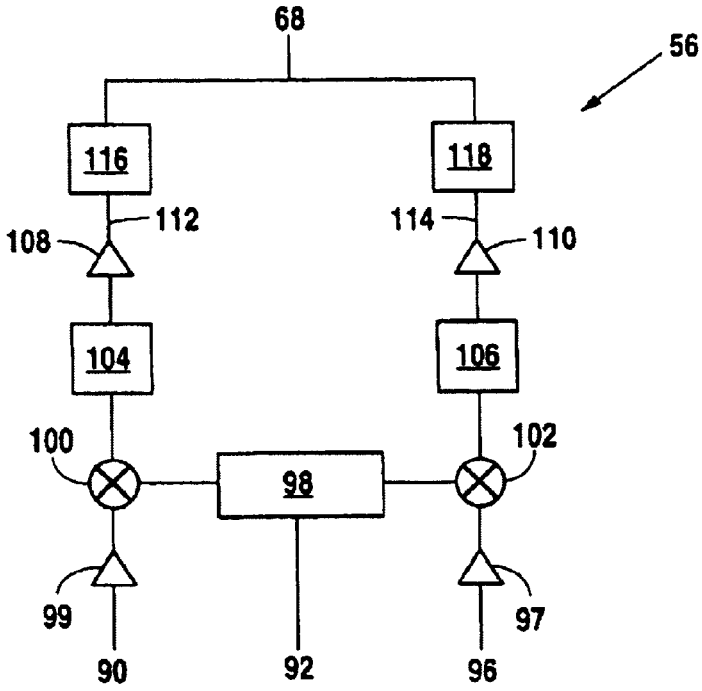
FIG. 6 is a block diagram of an embodiment of the present invention for processing an emitted signal.

FIG. 6 is a block diagram of the receiver component 56 of the present invention for processing the returned emitted signal. The present invention receives the modulated emitted signal 64 from the target mixture through a detector (60 of FIG. 7). The receiver component 56 receives the detected emitted signal 96 from the detector through an amplifier 97 and receives the driving/reference signal 90 through an amplifier 99. The receiver component 56 additionally receives the mixing signal 92 through a splitter 98. The present invention then mixes the detected emitted signal 96 with the mixing signal 92 with a mixer 102 and mixes the driving/reference signal 90 with the mixing signal 92 with a mixer 100. The resulting signals contain the sum and difference frequencies of the mixer's (100 and 102) input signals. The present invention generates a data signal 114 at 10 kHz by filtering the mixed detected emitted signal through a filter 106 with an amplitude 110 to eliminate the high frequency components. The present invention additionally generates a processor reference signal 112 at 10 kHz by filtering the mixed driving/reference signal through a filter 104 with an amplifier 108 to eliminate the high frequency components. One skilled in the art after reading this disclosure will appreciate that one can use frequencies other than 10 kHz to process signals. An analog to digital converter 118 converts the data signal 114 into digital data for transmittal over the digital I/O path 68 to the processor (50 of FIG. 4), and an analog to digital converter 116 converts the processor reference signal 112 into digital data for transmittal over the digital I/O path 68 to the processor. The present invention then processes the two input signals to determine their relative amplitudes and phases because the amplitude and phase of the 10 kHz signals are directly proportional to the amplitude and phase of the high frequency modulation signals. As the modulation frequency is stepped from 10 MHz to 200 MHz, the processor reference signal 112 and the data signal 114 remain at 10 kHz.

Figure 7:
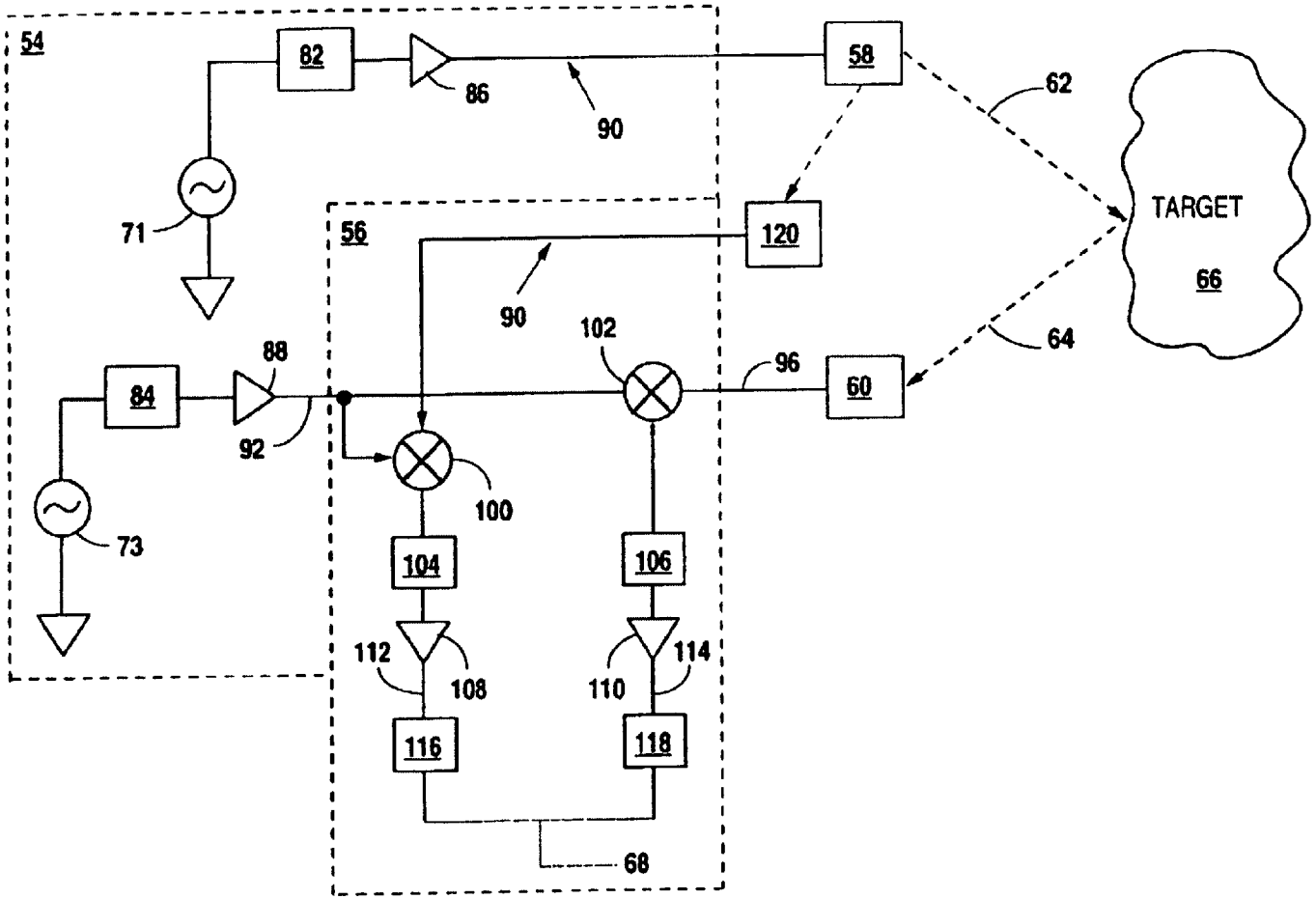
FIG. 7 is a block diagram of the present invention that illustrates the electrical pathways of the excitation signal and the emitted signal.

FIG. 7 is a block diagram of the present invention that illustrates the electrical pathways of the excitation signal and the emitted signal. The present invention generates the driving/reference signal with the driving/reference signal generator 71 and generates the mixing signal with a mixing signal generator 73. The present invention uses the driving/reference signal 90 to directly drive and modulate an excitation signal generator 58 that may comprise a laser diode, a light emitting diode (LED), or a Deuterium lamp. The present invention can also use the modulation to directly modulate an electro-optic crystal for use in external modulation of gas laser sources or other continuous emitting excitation light sources. The excitation signal generator 58 produces an excitation signal 62 that is transmitted to a target mixture 66. A photodetector 120 detects the excitation signal 62 on its way to the target and regenerates the driving/reference signal 90 for retransmission to the receiving component 56 of the present invention. The target mixture 66 absorbs the electronic energy of the excitation signal as the molecules of the target mixture move to a higher electronic energy state. During the fluorescence process, the molecules of the target mixture emit the emitted signal 64 as the molecules move to a lower electronic energy state. A detector 60 detects the emitted signal 64 from the target mixture 66. The detector 60 could comprise a photodetector. Additionally, wavelength dispersion of the emitted signal can be accomplished by using a spectrophotometer, monochromator or low-pass, high-pass and notch optical filters. From the detector 60, the present invention mixes the signals as previously described for FIG. 6 above. The present invention then uses a chemometric analysis to determine the individual fluorescence spectrum and fluorescence lifetime of one or more fluorophores within the target mixture 66.

The present invention comprises several techniques or alternative embodiments to "target" the target mixture. One embodiment of the present invention uses a target compartment for holding the target mixture within a chamber. A container may contain the target mixture, or the mixture may be free floating, in a fluid state, within the chamber. Another embodiment of the present invention uses an optical probe that combines the signal generator 58 and the detector 60 into a single probe. A user of the present invention would then probe or place the optical probe into the target mixture. And, another embodiment of the present invention may use a laser to target a free floating target mixture, such as the emission from a car (at a distance). One skilled in the art will appreciate that other embodiments of targeting the target mixture are possible after reviewing the disclosure of the present invention.

FIG. 8 is a block diagram of an embodiment of the present invention for a chemometric analysis of the emitted signal to determine the fluorescence spectrum and fluorescence lifetimes. Before discussing the block diagram of FIG. 8, we first need to discuss the mathematical foundation used for the chemometric analysis. Fluorescence occurs when a molecule, excited by a photon to a higher electronic state, decays non-radiatively to a lower vibrational level of the excited state, and then decays radiatively to a vibrational level of its ground electronic state. The non-radiative decay is assumed to be 'fast'. The characterization of the radiative decay is the fluorescence lifetime, $\tau$. And as previously stated, the wavelength of the fluorescent photon is greater (meaning less energy) than that of the exciting photon.

If we apply a 'monochromatic', short light pulse to the molecules of a fluorescent material at a time $t_0$, ideally represented by:

$$E(t)=E_0\cdot\delta(t-t_0) \tag{1}$$

where $E_0$ is the total energy in the pulse and E(t) is the intensity of the incident pulse as a function of time, we find that the fluorescent intensity at a fixed wavelength has the form:

$$I(t)=I_0 \quad e^{-(t-\omega)\kappa} \tag{2}$$

where $$I_0=\alpha\cdot E_0 \tag{3}$$

and $\alpha$ has appropriate units. Thus, by measuring the decay of the fluorescent intensity with time and fitting a straight line (linear least squares fit) to a graph of log(I(t)) vs time, we can determine the lifetime of a fluorophore. However, if more than one fluorophore is present, the intensity variation with time depends on the concentrations, $C_n$, and lifetimes, $\tau_n$, of the individual fluorophores:

$$I(t) = I_o\sum_n c_n e^{-(t-t_O)/\tau_n} \tag{4}$$

Now the intensity decay curve must be fit by a non-linear least squares process, which requires initial guesses for the number of fluorophores, r, their concentrations, and their lifetimes. In general, convergence of the solution cannot be guaranteed as it depends on the accuracy of the initial guesses.

Weber showed that decay constants and relative intensities of an arbitrary number of independence components in a heterogeneous fluorescence emission could, in principle, be determined by measuring phase shift and relative modulation of the total fluorescence at an equal number of frequencies. See Weber, G., Resolution of the Fluorescence Lifetimes in a Heterogeneous System by Phase and Modulation Measurements, J. Phys. Chem., 85, 949–953 (1981). At each frequency, the phase and modulation measurements yield the complex Fourier transform of the fluorescence impulse response, G+iS. The moments of a distribution of lifetimes are found as linear combination of the G's and S's and Prony's method is used to obtain lifetimes and concentrations of the components from the moments. Due to its sensitivity to noise, this method is really not practicable for more than binary mixtures.

Lackowicz and his coworkers developed an analysis of frequency domain phase and modulation data based on a weighted non-linear least square analysis. See Lackowicz, J. R., et al., Analysis of Fluorescence Decay Kinetics from Variable-Frequency Phase Shift and Modulation Data, Biophys. J., 46, 463–477 (1984). By taking data at several emission wavelengths, they were able to resolve binary mixtures whose components differed in lifetime by 30% and ternary mixtures the ratio of whose range of lifetimes spanned a decade. Best fit is determined by minimizing a reduced chi-squared function. Poor initial guesses can still produce unpredictable results.

Working with an Excitation-Emission-Frequency Array, McGown and her coworkers employed a principal components analysis followed by a non-linear least squares minimization on an over determined set of data to extract the spectra and lifetimes of components in a mixture. See Burdick, D. S., et al., Resolution of Multicomponent Fluorescent Mixtures by Analysis of the Excitation-Emission-Frequency Array, J. Chemometrics, 4, 15–28,(1990). In addition to requiring a non-linear minimization, a disadvantage of this method is that it requires evaluation over a large (3 dimensional) parameter space.

The present invention utilizes a novel system that uses a chemometric analysis for measuring the fluorescence lifetime and the fluorescence spectrum of a target mixture. Instead of irradiating the target sample with a single short pulse of light (photon counting) as other prior art systems, the present invention continuously irradiates the target mixture with a light source whose amplitude (intensity) and phase (frequency) are modulated (varied) with time. In evaluating experimental phase resolved fluorescent spectroscopy (PRFS) data, the variables sought are the concentrations, $c_i$, the lifetimes, $\tau_i$, and the emission spectra, $\alpha_i(\lambda)$, of the individual fluorescent contributors. The variables that we may control include the emission wavelength, $\lambda$, the modulation frequency, $\omega$, and the detector reference phase angle $\Phi_R$. We first consider an amplitude modulated excitation:

$$E(t)-E_0[1+M_e \sin(\omega t)],\ t>0 \tag{5}$$

where $\omega$ is the modulation angular frequency, $M_e$ is the modulation amplitude and $E_0$ is the average amplitude of the excitation.

At steady state, the modulated part of the fluorescent intensity may be given by $$I_\lambda(t)p=E_0M_eA \sin(\omega t-\Phi) \tag{6}$$

where A is the amplitude response at the fluorescent wavelength and $\Phi$ is the phase lag at this wavelength and frequency.

We originally detected this signal (the emitted signal) by correlating it with a reference signal (the driving/reference signal) by mixing the two signals with the mixing signal and integrating them over some multiple of a period. The correlated signal could therefore be expressed as:

$$\begin{aligned} S_\lambda(\omega, \Phi_R) &= \frac{\omega}{2\pi}\int_0^{\frac{2\pi}{\omega}} I_\lambda(t)\sin(\omega t-\Phi_R)dt \\ &= E_oM_eA\cos(\Phi_R-\Phi) \\ &= \frac{1}{2}E_oM_e\sum_{i=1}^{r}\varepsilon_i\cos\varphi_i\cos(\varphi_i-\Phi_R) \end{aligned} \tag{7}$$

where r is the number of components present (or fluorophores) and $\Phi_R$ is the phase of the reference signal relative to the backscattered excitation signal. We observe that $S_\lambda(\omega,\Phi_R)$ may be written as:

$$S_\lambda(\omega, \Phi_R) = \frac{1}{2}E_oM_e[G(\omega, \lambda)\cos\Phi_R + S(\omega, \lambda)\sin\Phi_R] \tag{8}$$

Therefore, as an alternative to Eqn. (8), we may determine $G(\omega,\lambda)$ and $S(\omega,\lambda)$ to within a common normalization factor, $E_0M_e/2$,for any fixed $\omega$ and $\lambda$ by making measurements at two different, but known, values of $\Phi_R$. In the presence of noise, more reference phase values would be used in the measurements and fit in a least squares manner to G and S.

We then find that for each value of $\omega$ and $\lambda$ (emission wavelength) we have (modulo the normalization factor):

$$G(\omega, \lambda) = \sum_i \varepsilon_i(\lambda)\cos^2\varphi_i(\omega) \tag{9}$$

$$S(\omega, \lambda) = \sum_i \varepsilon_i(\lambda)\cos\varphi_i(\omega)\sin\varphi_i(\omega) \tag{10}$$

with $\tan\phi_i=\omega\tau_i$, where i runs over the number of fluorophores present and assumed to be acting in an independent (uncorrelated) fashion.

The preferred embodiment of the present invention allows us to determine G and S by mixing the emitted signals from the mixture down to an intermediate frequency of 10 kHz, sample and digitize it at 50 kHz, Fourier transforming the result, and picking off the signal at 10 kHz. When this is done the mixed signal has the form:

$$I_\lambda(t)=E_0M_e[G \sin(\omega_H t)-S \cos(\omega_H t)] \tag{11}$$

From which we see that G and S are proportional to the Fourier transform of Equation (11).

In the case of noiseless data, where r fluorophores are present, it is necessary to make measurements at r values of $\lambda$ and r values of $\omega$ to obtain:

$$G-cc\cdot A \text{ and } S=cs\cdot A, \tag{12}$$

where $$\begin{aligned} &G=[G_{jk}] \\ &S=[S_{jk}] \\ &cc=[\cos^2\phi_r(\omega_j)]=[cc_{rj}] \\ &cs=[\cos\phi_i(\omega_j)\sin\phi_i(\omega_j)]=[cs_{ji}] \\ &A=[\epsilon_i(\lambda_k)]=[\alpha_{ik}] \end{aligned} \tag{13}$$

where the quantities defined in boldface are matrices. The matrix indices i, j, and k run over the components, the modulation frequencies, and the emission wavelengths, respectively.

If no noise is present, we may take the indices i, j, and k above to run from 1 to r, the number of components. As the fluorophores are assumed to be independent and as the frequencies $\{\omega_j\}$ may be chosen arbitrarily, all the matrices defined above have true inverses. Thus, from Eqns. (12) and (13) we find:

$$cc^{-1}G=A \tag{14}$$

and $$S=cs\cdot cc^{-1}\cdot G$$

or $$S\cdot G^{-1}\cdot cc=cs$$

Now, we note that:

$$\begin{aligned} cs &= [\cos\phi_i(\omega_j)\sin\phi_i(\omega_j)] \\ &= w\cdot cc\cdot T \end{aligned} \tag{15}$$

By substitution from $\tan\phi_i=\omega\tau_i$, we have:

$$\begin{aligned} cs &= [(\cos\phi_i(\omega_j))^2\omega_j\tau_i] \\ &= w\cdot cc\cdot T \end{aligned} \tag{16}$$

where $w=\mathrm{diag}[\omega_i]$ and $T=\mathrm{diag}[\tau_i]$. Hence, we find $$S\cdot G^{-1}\cdot cc=w\cdot cc\cdot T \tag{17}$$

or $$w^{-1}\cdot S\cdot G^{-1}\cdot cc=cc\cdot T$$

This equation is in the form of a standard eigenvalue/eigenfunction equation, where the $\tau_i$ are the eigenvalues and the columns of cc are the eigenfuctions. We may also write this in the form:

$$cc^{-1}\cdot w^{-1}\cdot S\cdot G^{-1}\cdot cc=T \text{ tm} \tag{18}$$

From which we have:

$$det(w^{-1}\cdot S\cdot G^{-1})=\prod_{i=1}^{r}\tau_i \text{ and} \tag{19}$$

$$Tr(w^{-1}\cdot S\cdot G^{-1})=\sum_{i=1}^{r}\tau_i \tag{20}$$

Since $\phi_i(\omega_j)$ is known once $\tau_i$ is know, we may determine cc or cs and solve the equation:

$$G=cc\cdot A \text{ or } S=cs\cdot A \tag{21}$$

for A with a standard LU decomposition, which gives us $$A=T^{-1}\cdot ccpi\cdot w^{-1}S \tag{22}$$

where ccpi is the pseudo inverse of cc.

Another, equivalent, way of writing the eigenfunction equations proceeds from the observation that:

$$G\cdot A^{-1}=C \tag{23}$$

and $$S=cs\cdot A=W\cdot cc\cdot T\cdot A \tag{24}$$

so that $$w^{-1}\cdot S\cdot A^{-1}=cc\cdot T=G\cdot A^{-1}\cdot T \tag{25}$$

or $$[G^{-1}\cdot w^{-1}S\cdot A^{-1}=A^{-1}\cdot T]\ G^{-1}\cdot w^{-1}\cdot S\cdot A^{-1}=A^{-1}\cdot T \tag{26}$$

Solving this eigenequation determines $\tau_i$ a the eigenvalues and $A^{-1}$ as the eigenvectors. However, as the eigenvectors are normalized, A may be better determined as above if information about the component concentrations is required.

Once the spectrum and lifetime of each component is known, as may use the information to identify the fluorophore. The concentration of each fluorophore may then be determined by comparing its spectrum against its standard spectrum. We find:

$$\frac{c_i}{c_j}=\frac{\varepsilon_i(\lambda)/\alpha_i(\lambda)\tau_i}{\varepsilon_j(\lambda)/\alpha_j(\lambda)\tau_j} \text{ with } \sum_i c_i=1, \tag{27}$$

where $\alpha_i(\lambda)$ is the standard spectral value of the ith component at wavelength $\lambda$ and $\tau_i$ is its lifetime.

The number of components in a mixture may not be known a priori, and the method requires the number of frequencies and wavelengths employed to at least equal the number of components. Furthermore, some degree of noise will be present in the experimental data. Therefore, it is useful to determine a means of solving for lifetimes and spectra when the number of frequencies and the number of emission wavelengths are unequal and when each is greater than the number of independent components present in the mixture.

In the following, we shall therefore assume that r components are present in a mixture, for which we have taken data a N frequencies and M emission wavelengths. We assume that $N,M\leqq r$ and that $N\neq M$, in general.

From Eqns. (12) and (16), we therefore have:

$$G=cc\cdot A \tag{28}$$

$$(N\times M)-(N\times r)-(r\times M)$$

and $$S=w\cdot cc\cdot T\cdot A \tag{29}$$

$$(N\times M)\cdot(N\times N)\cdot(N\times r)\cdot(r\times r)-(r\times M)$$

where the number of rows and columns of each matrix is indicated below it. In the noise free case, all the matrices are of rank r. In the presence of noise, G and S will be of rank N or M, whichever is smaller.

In the absence of noise, all matrices are of rank r. We manipulate Eqns. (28) and (29) slightly, to write:

$$G=cc\cdot I\cdot A$$

and $$w^{-1}\cdot S=cc\cdot T\cdot A \tag{30}$$

where I is the r×r identity matrix.

We may now make a singular value decomposition on the first of Eqns. (30):

$$G=U\cdot C_1\cdot V^T \tag{31}$$

$$(N\times M)\cdot(N\times r)\cdot(r\times r)\cdot(r\times M)$$

where $C_1$ is the diagonal matrix of singular values of G and U and V are each column orthonormal, i.e.:

$$U^T\cdot U=V^T\cdot V=I. \tag{32}$$

From Eqns. (31) and (32), we have:

$$C_1=U^T\cdot G\cdot V \tag{33}$$

We define:

$$C_2=U^T\cdot w^{-1}\cdot S\cdot V \tag{34}$$

where $C_2$ is not diagonal, in general, but is r×r.

It may easily be shown, by a process that is similar to Gram-Schmidt orthogonalization, that while, in general, neither matrix is invertible, cc has a left inverse and A has a right inverse:

$$ccli\cdot cc=I \text{ and } A\cdot Ari=I \tag{35}$$

From Eqns. (30) and (31), we may therefore write:

$$cc=U\cdot P_u \text{ and } A=P_v\cdot V^T \tag{36}$$

with $$P_U=C_1\cdot V^T\cdot Ari \text{ and } P_v=ccli\cdot U\cdot C_1.$$

where $P_U$ and $P_v$ are each r×r.

We may interpret the first of Eqns. (36) in terms of its column vectors as the representation of the r vectors of cc in the orthonomral basis of the r vectors of U:

$$c_j=\sum_{i=1}^{r}U_iP_{ij} \tag{37}$$

where $[c_j]$ $c_j$ is the jth column of cc, $[U_i]$ $U_i$ is the ith column of U and $P_{ij}$ is the corresponding element of $P_u$. From this expression and the linear independence of the $[c_j]$ $c_j$ and $[U_i]$ $U_j$, we see that $P_u$ is invertible. Linear independence of the [$c_j$] $c_j$ requires that:

$$\sum_{j=1}^{r} \alpha_j c_j = 0 \text{ only if } \alpha_j = 0 \text{ for all } j = 1, \ldots, r. \tag{38}$$

From Eqn. (36), we see that Eqn. (37) implies:

$$\sum_{i,j=1}^{r} U_i P_{ij} \alpha_j = 0.$$

From the linear independence of the [$U_i$] $U_j$, we must have $$\sum_{j=1}^{r} P_{ij} \alpha_j = 0, \text{ for all } i = 1, \ldots, r. \tag{39}$$

Thus, if the condition of Eqn (37) is to be satisfied, the system of Eqns. (39) must have only the trivial solution. This is equivalent to the requirement that $$\det [P_U] \neq 0.$$

Therefore, $P_U$ has an inverse. A similar argument shows that $P_v$ is also invertible.

From Eqns. (30), (33) and (34), we have:

$$C_2 = P_U \cdot T \cdot P_v \text{ and } C_1 = P_u \cdot I \cdot P_v. \tag{40}$$

Therefore, we may write:

$$C_1^{-1} \cdot C_2 = P_v^{-1} \cdot T \cdot P_v \tag{41}$$

or $$C^{-1} \cdot C_2 \cdot P_v^{-1} = P_v^{-1} \cdot T. \tag{42}$$

Eqn. (42) is the eigenvalue equation for the matrix, $C_1^{-1} \cdot C_2$, with the eigenvalues equal to the diagonal elements of T, and eigenvectors proportional to the column vectors of $P_v^{-1}$. The spectrum, A, may be determined from Eqns. (13) and (30) since cc is determined once the lifetimes are known.

A second method for solving Eqns. (30) is to use Eqn. (31) to write the pseudo inverse of G:

$$Gpi = V \cdot C_1^{-1} \cdot U^T \tag{43}$$

so that we have:

$$G \cdot Gpi = U \cdot U^T \text{ and } Gpi \cdot G = V \cdot V^T,$$

where $U \cdot U^T$ is [and] *an* N×N matrix and $V \cdot V^T$ is an M×M matrix, and each of these matrices is of rank r.

From Eqns. (30) and (35), we may write:

$$Gpi = V \cdot C_1^{-1} \cdot U^T \tag{44}$$

Substituting this into the first of Eqns. (30), we have:

$$Gpi \cdot w^{-1} \cdot S \cdot Ari = V \cdot V^T \cdot Ari \cdot T \tag{45}$$

From Eqns. (30) and (36) we have:

$$w^{-1} \cdot S = U \cdot P_u \cdot T \cdot P_v \cdot T. \tag{46}$$

From Eqn. (32), we therefore find:

$$w^{-1} \cdot S = w^{-1} \cdot S \cdot V \cdot V^T.$$

Substituting this into Eqn. (45), we therefore have:

$$Gpi \cdot w^{-1} \cdot S \cdot V \cdot V^T \cdot Ari = V \cdot V^T \cdot Ari \cdot T \tag{47}$$

Eqn. (47) is the eigenvalue equation for the matrix, $Gpi \cdot w^{-1} \cdot S$, with eigenvalues equal to the diagonal elements of T and eigenvectors proportional to the columns of $V \cdot V^T \cdot Ari$. The spectra, A, may be found as described above.

When determining the lifetimes, we can renormalize Eqn. (47) by using $$\text{pseidoinv}(g)\ w^{-1} S\ evec = evec\ T \tag{48}$$

where $evec = V \cdot V^T \cdot Ari$ for $T = \text{diag}(\tau_1, \ldots, \tau_r)$ For the case when noise is present, let us assume that r components are actually present, and let us take N<M. The experimentally determined matrices, Gx and Sx, are therefore of rank N. We wish to determine the N×M matrices, G and S, of rank r that minimize some suitably defined error.

We shall define the Euclidean norm of a matrix, M, to be given by:

$$\|M\|^2 = Tr(M^T \cdot M) = Tr(M \cdot M^T) = \sum_i \sum_j |m_{iu}|^2 \tag{49}$$

The error we define will depend on our knowledge of the statistics of the experimental data. We shall assume that the errors at each data point are uncorrelated with those at our data points and that the standard deviations from the sample means are the same for all data points. This is tantamount to the assumption that the statistics are independent of the modulation frequency and the emission wavelength for the ranges of the variables explored. Previous experience with experimental data tends to bear this assumption out.

Given these assumptions, it is reasonable to define the error, $\chi^2$, in terms of the equally weighted distance of the experimental points from their analytical counterparts, i.e.:

$$\chi^2 = \|Gx - G\|^2 + \|w^{-1} \cdot Sx - w^{-1} \cdot S\|^2 \tag{50}$$

where G satisfies Eqn. (31) and where, from Eqns. (40) and (46), we see that S satisfies:

$$w^{-1} \cdot S = U \cdot C_2 \cdot V^T \tag{51}$$

Therefore, from Eqns. (31), (50) and (51), we must find U, V, $C_1$ and $C_2$ to minimize:

$$\chi^2 = \|Gx - U \cdot C_1 \cdot V^T\|^2 + \|w^{-1} \cdot Sx - U \cdot C_2 \cdot V^T\|^2 \tag{52}$$

Minimizing Eqn. (52) will yield a least squares fit for the data.

For Eqn. (52) to be a minimum, its partial derivatives with respect to each free variable must vanish. Applying this requirement with respect to the variables of $C_1$, we find:

$$C_1 = U^T \cdot Gx \cdot V \tag{53}$$

or, from Eqn. (31), $$G = U \cdot U^T \cdot Gx \cdot V^T = Q_u \cdot Gx \cdot Qv \tag{54}$$

where $$Q_u = U \cdot U^T \text{ and } Q_v = V \cdot V^T \tag{55}$$

Proceeding similarly for the variables of $C_2$, we find:

$$C_2=U^T\cdot w^{-1}\cdot Sx\cdot V \quad (56)$$

$$\text{or } w^{-1}\cdot S=Q_u\cdot w^{-1}\cdot Sx\cdot Q_v \quad (57)$$

$$\text{or } =U\cdot U^T\cdot w^{-1}\cdot S\cdot Vx\cdot V^T \quad (58)$$

Eqns. (54) and (57) determine $C_1$ and $C_2$ once U and V are determined. We now proceed to determine these variables.

By substituting for G and $w^{-1}S$ from Eqns. (54) and (57) into Eqn. (50), we find that minimizing that expression implies that we must maximize:

$$\eta=\|Q_u\cdot Gx\cdot Qv\|^2+\|Q_u+w^{-1}\cdot Sx\cdot Q_v\|^2 \quad (59)$$

or $$\eta=\mathrm{Tr}(gg^T)+\mathrm{TR}[(w^{-1}S)(w^{-1}S)^T] \quad (60)$$

Observing that:

$$Q_u=Q_u^T,\ Q_u\cdot Q_u=Q_u, \quad (61)$$

$$\text{and } Q_v=Q_v^T,\ Q_v\cdot Q_v=Q_v, \quad (62)$$

we may rewrite Eqn. (59) in the alternative forms:

[$\eta=\mathrm{Tr}(M_v\cdot U\cdot U_T)$]

$$\eta=Tr(M_V\cdot U\cdot U^T) \quad (63)$$

$$\text{or } \eta=\mathrm{Tr}(M_u\cdot V\cdot V^T) \quad (64)$$

$$\text{where } M_v=Gx\cdot Q_v\cdot Gx^T+(w^{-1}\cdot Sx)\cdot Q_v\cdot(w^{-1}\cdot Sx)^T \quad (65)$$

$$\text{and } M_U=Gx^T\cdot Q_U\cdot Gx+(w^{-1}\cdot Sx)^T\cdot Q_U\cdot(w^{-1}\cdot Sx) \quad (66)$$

We note that $M_v$ is an N×N matrix, $M_U$ is an M×M matrix, and both matrices are symmetric.

If we assume that V is known, we may determine U by requiring that it be chosen to maximize Eqn. (63) subject to the constraint imposed by Eqn. (32). We may solve for U by means of Lagrange multipliers.

$$\text{Define: } \eta^1=\eta-\mathrm{Tr}[L_v\cdot(U^T\cdot U-I)] \quad (67)$$

where $L_v$ is a symmetric r×r matrix formed from the multipliers.

We may now extremize η' with U unconstrained to find:

$$M_v\cdot U=U\cdot L_v \quad (68)$$

Since it is symmetric, $L_v$ may be diagonalized by a similarity transform with an appropriate orthogonal matrix. Therefore, we may write:

$$M_v\cdot U=U\cdot O\cdot D\cdot O^{-1} \quad (69)$$

where D is an r×r diagonal matrix and O is an r×r orthogonal matrix.

We may then write:

$$(M_v=U\cdot O=U\cdot O\cdot D \quad (70)$$

Substituting Eqn. (70) into Eqn. (63) we find:

$$\eta=\mathrm{Tr}(M_v\cdot U\cdot O\cdot O^{-1}\cdot U^T)$$

$$=\mathrm{Tr}[(U\cdot O)\cdot D\cdot(U\cdot O)^T]$$

$$=\mathrm{Tr}[D\cdot(U\cdot O)\cdot(U\cdot O)]$$

or, finally, $$\eta=\mathrm{Tr}(D) \quad (70)$$

Thus, to maximize η we choose U to maximize D as determined by Eqn. (70). We may easily do this by observing that Eqn. (70) has the form of an eigenvalue equation. The matrix D yields r of the N possible eigenvalues of the matrix $M_v$. We therefore solve the eigenvalue equation for $M_v$:

$$M_v\cdot\hat{U}=\hat{U}\cdot E \quad (71)$$

taking the largest r eigenvalues of E for D and, without loss of generality, choosing U to equal the corresponding eigenvectors of U.

A similar procedure may be used to determine V from Eqn. (64) if U is known using the relationship $M_U\cdot V=L_U$ to find $L_U$.

FIG. 8 is a block diagram of the preferred embodiment of the present invention that uses the above foundation as a basis for a chemometric analysis of the emitted signal to determine the fluorescent spectrum and fluorescence lifetimes. The present invention first acquires the data from the data signal and the reference signal to determine the frequency and wavelength vectors 132. Next, the present invention assumes an arbitrary but fixed number of fluorophores, r, 134. We then determine the initial G and S matrices 136.

As the frequencies in w are large, we renormalize $\|w^{-1}\cdot Sx\|$ to equal $\|Gx\|$ so as to avoid skewing the results in favor of the Gx data 138. This amounts to a [resealing] *rescaling* of the units for the frequencies and the lifetimes. This [resealing] *rescaling* of units is compensated once the lifetimes are found, so they are expressed in seconds.

We begin the iterative approach by determining the initial approximations for U, V, g and $w^{-1}$s approximations 140, 142, and 144. The initial iteration begins by choosing the r columns of $U_1$ to be the eigenvectors corresponding to the r largest eigenvalues of the matrix $$Gx\cdot Gx^T+(w^{-1}\cdot Sx)\cdot(w^{-1}\cdot Sx)^T \quad (73)$$

$$\text{or } [G\cdot G^T+(w^{-1}\cdot S)\cdot(w^{-1}\cdot S)^T]\cdot U=UL \quad (74)$$

where $L=\mathrm{diag}(\lambda_1, \ldots, \lambda_T)$ for $\lambda_1> \ldots \lambda_T$. Next, U is used to form the matrix $M_{U1}$ in accordance with Eqn. (66). We can determine $V_1$ from $M_{U1}$ by solving the eigenfunction equation $M_{U_1}\cdot V=V\cdot L_U$ by choosing its r columns to be the eigenvectors corresponding to the r largest eigenvalues of $M_{U1}$. We then form $M_{V1}$ in accordance with Eqn. (65).

We next initialize the decision variables 146 to produce the solution in a reasonable time, with a reasonable accuracy, and a reasonable number of iterations. We begin the iterative solution by comparing the decision variables 148 for convergence to see if further determinations for U, V,g and $w^{-1}$s are necessary as above. In the iterative solution, we proceed to maximize η, given by Eqn. (59), and recognizing that:

$$0\leq\eta\leq\|Gx\|^2+\|w^{-1}\cdot Sx\|^2=N \quad (72)$$

Proceeding in this way, we form a sequence of η values $\{\eta_i\}$. We see easily that the sequence is monotonic nondecreasing. By Eqn. (72) and the Bolzano-Weierstrass theorem, the sequence has at least one limit point in the interval [0,N]. The monotonic nature of the sequence guarantees that there can be cut one limit point. Therefore the sequence must converge.

The values of U and V corresponding to the limit of the sequence are then used to form G and $w^{-1}S$ in accordance with Eqns. (54) and (57). Eqn. (47) may subsequently be solved for the lifetimes and spectra as described previously 160, 162, and 164.

In the preceding, we assumed an arbitrary but fixed value, r, for the number of fluorescing components present. Fits to the data may be found for different values of r. The question then arises as to the value of r that best fits the experimental data. Two qualitative criteria may be stated: (1) the spectra should look reasonable; and (2) the lifetime should be positive real numbers.

Somewhat more quantitatively, we recognize that $\chi^2$, suitably renormalized for frequency as described above, represents our error for a fixed value of r. However, the value of $\chi^2$ depends on the number of free parameters available for the fit, which, in turn, depends on r. Instead, we attempt to remove this dependence by dividing by the difference between the number of experimental data points and the number of free parameters present:

$$\chi_R^2 = \frac{\chi^2}{N_\chi - N_f} \tag{75}$$

where $\chi^2_R$ is the reduced error team, $N_x$ is the number of experimental data points and $N_f$ is the number of free parameters.

Since we collect an amplitude and a phase value for each emission wavelength and each modulation frequency, we have:

$$N_x = 2N_w N_\lambda \tag{76}$$

where $N_w$ is the number of frequencies and $N_\lambda$ is the number of wavelengths used.

From Eqns. (54), (57) and (68), we see that the free parameters being fit to the experimental data are the elements of U, V, $L_V$ and $L_U$ subject to the constraints of Eqns. (32). For r components, we therefore find that:

$$\begin{aligned} N_f &= r \cdot N_W + r \cdot N_\lambda + 2 \cdot \frac{1}{2} \cdot r(r+1) - 2 \cdot \frac{1}{2} \cdot r(r+1) \\ &= r \cdot N_W + r \cdot N_\lambda \end{aligned} \tag{77}$$

We evaluate $\chi^2_R$ for each r, and choose the value of r corresponding to the smallest value of $\chi^2_R$ to represent the number of components which best fits the data 158.

If two or more lifetimes are the same, their components will not be separable by this method, nor will they be separable by the method of PREEMSs. Their contributions will remain combined as that of a single component with the common lifetime and a spectrum given by the combined spectrum appropriate to their concentrations.

Figure 9:
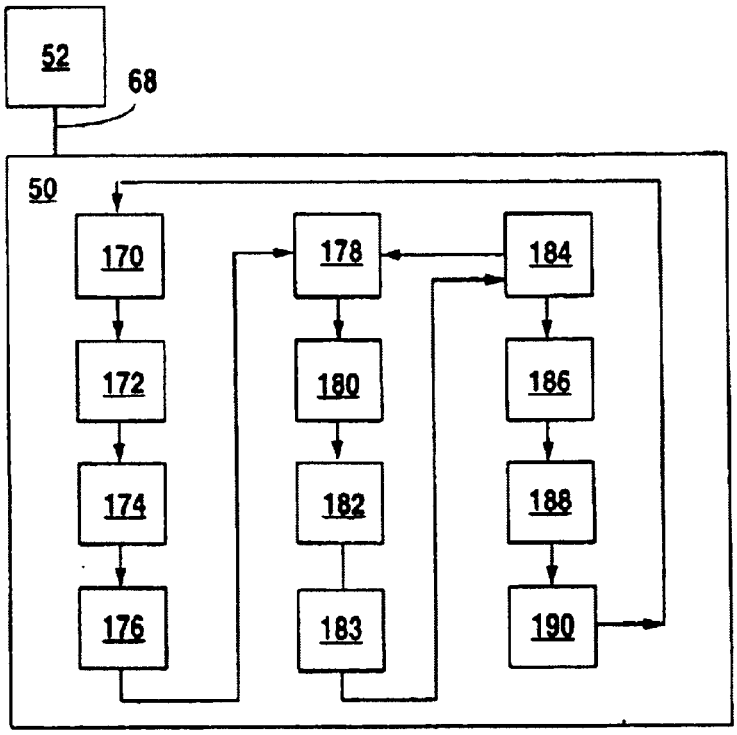
FIG. 9 is another block diagram of an embodiment of the present invention for a chemometric analysis of the emitted signal to determine the fluorescence spectrum and fluorescence lifetimes.

FIG. 9 illustrates an embodiment of the present invention for the method described in FIG. 8 for a chemometric analysis of the emitted signal to determine the fluorescence spectra and fluorescence lifetimes. The user interface 170 allows the user of the present invention to interact with the system of the present invention. The user interface allows the user to choose the number of components or fluorophores to solve for. The data acquisition component 172 uses the processor 50 coupled to a data gathering component through a data input/output path 68 to acquire the data from the emitted signal to determine the frequency and wavelength vectors. A determiner 174 determines the G and S matrices from the frequency and wavelength vectors. A renormalizer 176 then renormalizes $w^{-1}S_x$ to $G_x$. A determiner 178 next determines the initial U approximation, and a determiner 180 determines the initial V approximation, and a determiner 182 determines the initial g and $w^{-1}$s approximations. An initializer/updater 183 then initializes the decision variables. The iterative solution of the present invention uses a comparator 184 that compares the decision variables for convergence to see if further determinations for U, V, g and $w^{-1}$s are necessary. If the solution does not converge, the present invention uses the determiner 178 to determine the next U approximation, the determiner 180 to determine the next V approximation, and the determiner 182 to determine the next g and $w^{-1}$s approximations. The present invention then uses the initializer/updater 183 to update the decision variables.

When the solution converges, a determiner 186 determines the reduced best fit error for the analysis of the individual fluorescence lifetimes and fluorescence spectra. The present invention then uses an extractor 188 that extracts the individual fluorescence lifetimes from the target mixture, and an extractor 190 that extracts the individual fluorescence spectra.

Figure 10:
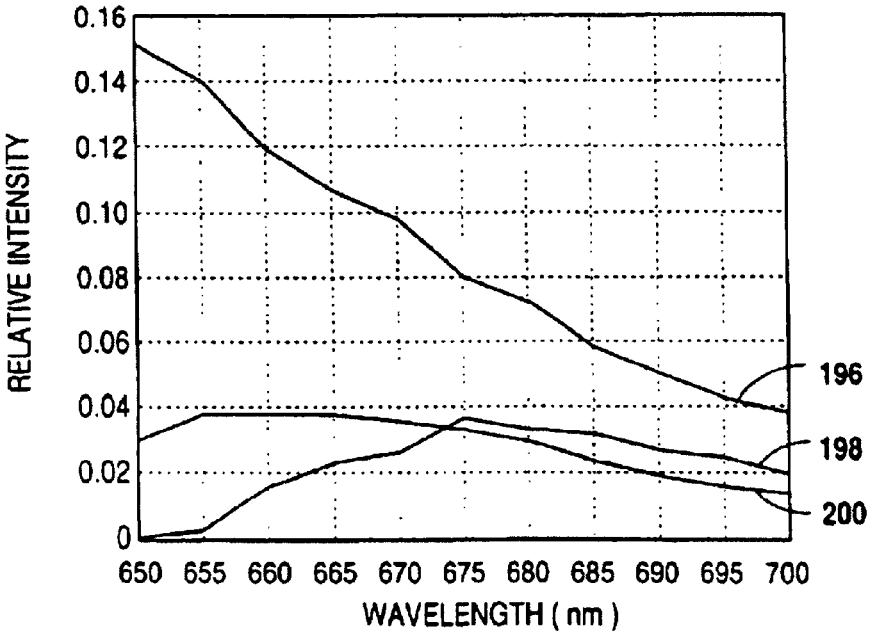
FIG. 10 illustrates the present invention's ability to differentiate spectra in a target mixture.

FIG. 10 illustrates the present invention's ability to identify and discriminate between individual overlapping spectral components in a target mixture. The present invention allows for the extraction of both the individual fluorescence spectra and lifetimes from a target mixture of fluorophores. FIG. 10 illustrates the present inventions ability to differentiate spectra using a three-dye mixture of OXAZINE™ 720, 725 and 750. OXAZINE is a trademark of Excition, Inc. We mixed the dyes at equal concentrations of 3.3 μM. We recorded the emission spectra for an excitation signal wavelength of 640 nm and the laser modulation frequency was swept (modulated) from 10 MHz to 140 MHz at 5 MHz increments. The present invention extracted fluorescence lifetimes of 3.705 nsec for Oxazine 720 (196 on FIG. 10), 1.979 nsec for Oxazine 750 [(] (198 on FIG. 10), and 0.5588 nsec for Oxazine 725 (200 on FIG. 10). The results from the present invention compared very well with the listed individual dye fluorescence lifetimes of 3.739 nsec for Oxazine 720, 2.014 nsec for Oxazine 750 and 0.9935 nsec for Oxazine 725. The individual spectra extracted for each dye from the mixture revealed spectral characteristics that matched with spectra obtained from the individual dyes.

The present invention overcomes the limitations of the prior art systems by utilizing a novel technique to measure the fluorescence lifetime. Instead of irradiating the target sample with a single short pulse of light, the present invention continuously irradiates the target sample with a light source whose amplitude and phase are modulated with time. This technique allows the present invention to use a chemometric analysis to automatically extract the lifetimes from the 'phase delay' and 'intensity vs. time' characteristics of the emitted light.

The present invention is a system for chemometric analysis for the extraction of the individual fluorescence spectrum and fluorescence lifetime from a target mixture. The present invention comprises a processor with an apparatus for generating an excitation signal to transmit at a target mixture and an apparatus for detecting the emitted signal from the target mixture. The present invention extracts the individual fluorescence spectrum and fluorescence lifetime measurements from the frequency and wavelength data acquired from the emitted signal. The present invention uses an iterative solution that first requires the initialization of several decision variables and the initial approximation determination of intermediate matrices. The iterative solution compares the decision variables for convergence to see if further approximation determinations are necessary. If the solution converges, the present invention then determines the reduced best fit error for the analysis of the individual fluorescence lifetime and the fluorescence spectrum before extracting the individual fluorescence lifetime and fluorescence spectrum from the emitted signal of the target mixture.

The present invention additionally comprises a method and apparatus for generating and mixing signals for frequency-domain lifetime and spectral fluorometry. The present invention comprises a plurality of signal generators that generate a plurality of signals where the signal generators modulate the amplitude and/or the frequency of the signals. The present invention uses one of these signals to drive an excitation signal that the present invention then directs and transmits at a target mixture, which absorbs the energy from the excitation signal. The property of fluorescence causes the target mixture to emit an emitted signal that the present invention detects with a signal detector. The present invention uses a plurality of mixers to produce a processor reference signal and a data signal. The present invention then uses a processor to compare the processor reference signal with the data signal by analyzing the differences in the phase and the differences in the amplitude between the two signals. The processor then extracts the fluorescence lifetime and fluorescence spectrum of the emitted signal from the phase and amplitude information using a chemometric analysis.

Other embodiments of the invention will be apparent to those skilled in the art after considering this specification or practicing the disclosed invention. The specification and example above are exemplary only, with the true scope of the invention being indicated by the following claims.

We claim:

1. An apparatus for fluorescence lifetime and spectral measurements, comprising:

a driving/reference signal generator that generates a driving/reference signal, said driving/reference signal is amplitude and/or frequency modulated over time;

a mixing signal generator that generates a mixing signal, said mixing signal is amplitude and/or frequency modulated over time;

an excitation signal generator that generates an excitation signal, the driving/reference signal drives said excitation signal generator;

a signal detector that detects the emitted signal;

a mixer that mixes the [emitted] *mixing* signal with the driving/reference signal and produces the processor reference signal;

a mixer that mixes the emitted signals with the mixing signal and produces the data signal; and a processor that extracts the fluorescence lifetime and fluorescence spectrum of the emitted signal from the comparison of the processor reference signal with the data signal using a chemometric analysis.

2. The apparatus of claim 1 wherein the driving/reference signal and the mixing signal vary by an adjustable offset frequency.

3. The apparatus of claim 1 wherein said chemometric analysis extracts the fluorescence lifetime of the emitted signal from the phase difference between the processor reference signal and the data signal.

4. The apparatus of claim 1 wherein said chemometric analysis extracts the fluorescence spectrum of the emitted signal from the amplitude difference between the processor reference signal and the data signal.

5. The apparatus of claim 1 wherein said chemometric analysis further comprises a converging iterative solution.

6. A system for fluorescence lifetime and spectral measurements, comprising:

means for generating a driving/reference signal, said driving/reference signal means modulates the amplitude and/or the frequency of the driving/reference signal over time;

means for generating a mixing signal, said mixing signal means modulates the amplitude and/or the frequency of the mixing signal over time, means for generating an excitation signal, the driving/reference signal drives said excitation signal means;

means for detecting the emitted signal;

means for mixing the [emitted] *mixing* signal with the driving/reference signal to produce the processor reference signal;

means for mixing the emitted signal with the mixing signal to produce the data signal; and a processor that extracts the fluorescence lifetime and fluorescence spectrum of the emitted signal from the comparison of the processor reference signal with the data signal using a chemometric analysis.

7. The system of claim 6 wherein the driving/reference signal and the mixing signal vary by an adjustable offset frequency.

8. The system of claim 6 wherein said chemometric analysis extracts the fluorescence lifetime of the emitted signal from the phase difference between the processor reference signal and the data signal.

9. The system of claim 6 wherein said chemometric analysis extracts the fluorescence spectrum of the emitted signal from the amplitude difference between the processor reference signal and the data signal.

10. The system of claim 6 wherein said chemometric analysis further comprises a converging iterative solution.

11. A method for forming the fluorescence lifetime and the fluorescence spectrum, comprising the following steps:

generating a driving/reference signal and modulating the amplitude and/or the frequency of the driving/reference signal over time;

generating a mixing signal and modulating the amplitude and/or the frequency of the mixing signal over time;

generating an excitation signal form the driving/reference signal;

detecting the emitted signal, mixing the [emitted] *mixing* signal with the driving/reference signal and producing the processor reference signal;

mixing the emitted signal with the mixing signal producing the data signal; and extracting the fluorescence lifetime and fluorescence spectrum of the emitted signal from the comparison of the processor reference signal with the data signal to measure using a chemometric analysis.

12. The method of claim 11 wherein the driving/reference signal and the mixing signal vary by an adjustable offset frequency.

13. The method of claim 11 wherein said chemometric analysis extracts the fluorescence lifetime of the emitted signal from the phase difference between the processor reference signal and the data signal.

14. The method of claim 11 wherein said chemometric analysis extracts the fluorescence spectrum of the emitted signal from the amplitude difference between the processor reference signal and the data signal.

15. The method of claim 11 wherein said chemometric analysis further comprises a converging iterative solution.

16. A method of producing an apparatus for fluorescence lifetime and spectral measurements, comprising:

providing a driving/reference signal generator that generates a driving/reference signal, said driving/reference signal is amplitude and/or frequency modulated over time;

providing a mixing signal generator that generates a mixing signal, said mixing signal is amplitude and/or frequency modulated over time;

coupling an excitation signal generator that generates an excitation signal and a reference signal to said driving/reference generator;

providing a signal detector that detects the emitted signal;

coupling a first mixer to said excitation signal generator, said mixer mixes the [emitted] *mixing* signal with the driving/reference signal to produce the processor reference signal, coupling a second mixer to said mixing signal generator, said mixer mixes the emitted signal with the mixing signal to produce the data signal; and coupling a processor to said first mixer and said second mixer, said processor extracts the fluorescence lifetime and fluorescence spectrum of the emitted signal from the comparison of the processor reference signal with the data signal using a chemometric analysis.

17. The method of claim 16 wherein the driving/reference signal and the mixing signal vary by an adjustable offset frequency.

18. The method of claim 16 wherein said chemometric analysis extracts the fluorescence lifetime of the emitted signal from the phase difference between the processor reference signal and the data signal.

19. The method of claim 16 wherein said chemometric analysis extracts the fluorescence spectrum of the emitted signal from the amplitude difference between the processor reference signal and the data signal.

20. The method of claim 16 wherein said chemometric analysis further comprises a converging iterative solution.

21. A program storage device readable by a computer, tangibly embodying a program of instructions executable by the computer to perform method steps for a method for measuring the fluorescence lifetime and the fluorescence spectrum, comprising the following method steps:

generating a driving/reference signal and modulating the amplitude and/or the frequency of the driving/reference signal over time;

generating a mixing signal and modulating the amplitude and/or the frequency of the mixing signal over time;

generating an excitation signal from the driving/reference signal;

detecting the emitted signal;

mixing the [emitted] *mixing* signal with the driving/reference signal and producing the processor reference signal;

mixing the emitted signal with the mixing signal producing the data signal; and extracting the fluorescence lifetime and fluorescence spectrum of the emitted signal from the comparison of the processor reference signal with the data signal to measure using a chemometric analysis.

22. The program storage device of claim 21 wherein the driving/reference signal and the mixing signal vary by an adjustable offset frequency.

23. The program storage device of claim 21 wherein said chemometric analysis extracts the fluorescence lifetime of the emitted signal from the phase difference between the processor reference signal and the data signal.

24. The program storage device of claim 21 wherein said chemometric analysis extracts the fluorescence spectrum of the emitted signal from the amplitude difference between the processor reference signal and the data signal.

25. The program storage device of claim 21 wherein said chemometric analysis further comprises a converging iterative solution.

* * * * *